United States Patent [19]

Brackenridge

[11] 4,013,728
[45] Mar. 22, 1977

[54] PROCESS FOR HALOGENATING A BISPHENOL

[75] Inventor: David R. Brackenridge, Royal Oak, Mich.

[73] Assignee: Ethyl Corporation, Richmond, Va.

[22] Filed: Apr. 5, 1976

[21] Appl. No.: 673,387

Related U.S. Application Data

[63] Continuation-in-part of Ser. No. 281,851, Aug. 18, 1972, abandoned.

[52] U.S. Cl. .................. 260/619 A; 260/619 R; 260/623 H
[51] Int. Cl.[2] .......................... C07C 37/00
[58] Field of Search ........ 260/619 R, 621 R, 623 H

[56] References Cited

UNITED STATES PATENTS 3,234,289  2/1966  Hennis .................... 260/619 A

FOREIGN PATENTS OR APPLICATIONS 1,129,957  12/1962  Germany ................. 260/619 A
614,235  12/1948  United Kingdom ........... 260/619 A

OTHER PUBLICATIONS

Zincke, "Ann," vol. 343, p. 86, (1905).

*Primary Examiner*—Norman Morgenstern
*Attorney, Agent, or Firm*—Donald L. Johnson; John F. Sieberth; Robert A. Linn

[57] ABSTRACT

Halogenated bisphenols, such as 4,4'-isopropylidenebis(2,6-dibromophenol), can be produced in high purity and high yield by brominating in 75–95 weight per cent aqueous acetic acid, and subsequently heating the reaction mass at 80° – 120° C. for 5–60 minutes. The resultant mixture can be neutralized prior to separating desired product from the reaction mixture.

11 Claims, No Drawings

PROCESS FOR HALOGENATING A BISPHENOL

CROSS-REFERENCE TO RELATED APPLICATION

This application is a Continuation-in-Part of Application Serial No. 281,851, filed August 18, 1972 now abandoned.

BACKGROUND OF THE INVENTION

Zincke et al, Ann. 343 86 (1905) used acetic acid to prepare alkylidene bis(dibromophenol) and recovered a product having a melting point of 162°–163° C. In British patent No. 614,235, the melting point is given as about 160°–161° C.

British patent No. 1,031,500 indicates that with glacial acetic acid after a reaction time of 1 to 2 days, the desired bromine derivative is separated from the mother liquor with a yield of 70–78 percent as an impure raw material which must be purified by recrystallizing.

German patent No. 1,129,957 describes bromination of bisphenol-A in 70–100 percent acetic acid using a mixture of bromine and chlorine as the brominating agent. German patent No. 1,151,811 also teaches use of the same solvent and brominating agent.

U.S. Pat. No. 3,234,289 teaches use of a post-heating step when tetrabromobisphenols are made by bromination in an alkanol-water solvent.

Using the process of this invention, I have prepared 4,4'-isopropylidene bis(2,6-dibromophenol) with a melting point as high as 180°–182° C.

SUMMARY OF THE INVENTION

This invention pertains to a process for producing an alkylidene bis(dibromophenol), said process comprising a bromination step and a post-heating step; said bromination step comprising reacting bromine and an alkylidene bisphenol having the formula

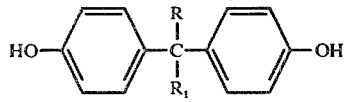

wherein R and $R_1$ are independently selected from the class consisting of hydrogen and alkyl groups of from 1 to about 3 carbons, in a water-acetic acid mixture, the concentration of acetic acid being from about 75 to about 95 weight percent; and said post-heating step comprising subsequently heating the thereby-produced reaction mixture at a temperature of from about 80° to about 120° C for a period of from about 5 to about 60 minutes.

In a preferred embodiment, the starting phenol is bisphenol-A, i.e., p,p'isopropylidenediphenol. Preferably, the bromination step is conducted at a temperature of from about 0 to about 30° C. The post-heating step is preferably conducted at from about 80° to about 120° C for from about 5 to about 60 minutes.

Optionally, the post-heated reaction mixture can be neutralized or partially neutralized prior to isolating the desired reaction product. This is carried out by adding the desired amount of alkaline substance to the post-heated reaction mixture. Preferred alkaline substances are sodium hydroxide and sodium carbonate. Since the aqueous-acetic acid mixture can be recycled, it is preferred to add an amount of alkaline substance substantially equal to the amount required to neutralize HBr present in the post-heated reaction mixture.

Thus, in a highly preferred embodiment, this invention pertains to a process for producing tetrabromo bisphenol-A, said process comprising
 a. brominating bisphenol A at 20°–30° C. in aqueous acetic acid reaction medium, the concentration of acetic acid in the acetic acid-water mixture being from about 80 to about 90 weight percent, then
 b. over a period of about 30 to about 60 minutes, raising the temperature to a post-heating temperature of from about 100°–110° C. and maintaining said post-heating temperature for from about 20 to about 30 minutes,
 c. subsequently adding an amount of alkaline substance substantially equal to that required to neutralize the HBr present in the heated mixture, the substance being selected from sodium hydroxide and sodium carbonate, and
 d. separating the thus-purified tetrabromo bisphenol-A, from the alkaline substance-treated reaction mixture.

Brominated phenols such as 4,4'-isopropylidene bis(2,6-dibromophenol) i.e. tetrabromo bisphenol-A, can be used for making flame retardant epoxy resins; U.S. Pat. Nos. 3,016,362, 3,058,946, and 3,268,619.

DESCRIPTION OF PREFERRED EMBODIMENTS

As stated above, this process involves reaction of halogen with a bisphenol

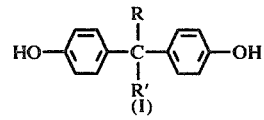

wherein R and R' are independently selected from hydrogen and alkyl radicals of one to about three carbon atoms. Typical phenols are
 i. 4,4'-methylene bis(phenol)
 ii. 4,4'-ethylene bis(phenol)
 iii. 3,3'-di-(4-hydroxyphenyl)-sec-butane
 iv. 1,1-di-(4-hydroxyphenyl)-n-propane
 v. 1,1-di-(4-hydroxyphenyl)-n-butane
 vi. 2,2-di-(4-hydroxyphenyl)-n-butane
 vii. 3,3-di-(4-hydroxyphenyl)-n-pentane
 viii. 2,2-di-(4-hydroxyphenyl)-n-pentane
 ix. 4,4-di-(4-hydroxyphenyl)-n-heptane
 x. 3,3'-di-(4-hydroxyphenyl)-n-hexane A preferred compound is 2,2-di-(4-hydroxyphenyl)-n-propane, i.e., bisphenol-A.

Of the halogens, chlorine and bromine are preferred, with bromine being most preferred. About 4 moles of halogen are used per each mole of diphenol. There is no real upper limit on the amount of bromine used, this being defined by such secondary considerations as economics, size of the reaction vessel, etc. In general, an excess of bromine is used to assist forcing the reaction to completion. Thus, good results are obtained when 4 to 5 moles of bromine are used per mole of diphenol.

Aqueous acetic acid gives better results than glacial acetic acid. Good results are obtained when the concentration of acetic acid is from about 75 to about 95 weight percent. A more preferred range is from about 80 to about 90 weight percent.

There is no real upper or lower limit on the amount of acid-water mixture used. Generally, one uses enough water and acid to obtain a reaction mixture that can readily be stirred and which has enough fluidity to afford ready contact of the reactants. Likewise, one does not wish to use more reaction medium than that which is economical and convenient for the size of the reaction vessel employed. In general, one uses from about 70 to about 300 grams of acetic acid -- in water as set forth above -- per each 100 gram portion of bisphenol. A more preferred range is from about 120 to about 200 grams of acetic acid per 100 gram portion of diphenol.

The applicability of acetic acid suggests that comparable aqueous mixtures of other organic acids can also be used. Such acids are exemplified by formic, propionic, n-butyric, isobutyric, oxalic, and the like.

The reaction temperature for the halogenation step is not critical. Generally, a temperature is used which affords a reasonable rate of reaction without an untoward amount of decomposition or by-product formation. Ambient temperatures, or temperatures slightly above or below ambient are generally employed. Generally, temperatures of from about −10° to about 40° C. are employed. A preferred range is from 0° to about 30° C. A more preferred range is 20°-25° C.

The process pressure is not critical and any desired pressure can be used. Ambient pressure is convenient and affords good results.

The reaction time is not a truly independent variable and is dependent at least to some extent on the other reaction conditions employed. In general, good results are obtained when a bromination step is conducted over a period of from about ½ to about 3 hours. If desired, the bromine can be added over a first portion of the bromination period and the bromination temperature maintained for the remainder of the bromination step.

If desired, the reaction can be conducted under an inert atmosphere. The atmosphere can be made by a substantially continuous or intermittent inert gas addition into the reaction zone. Nitrogen or other inert gas can be used. It is to be understood, however, that neither use of an inert gas nor introduction during or over the reaction period is required.

After reaction with bromine, the reaction mass is raised to a post-heating temperature. Preferably, the temperature is raised over an appreciable period, say ½ to 1 hour. The post-heating temperature is from about 80 to about 120° C. A more preferred temperature is from about 100° to about 110° C. The post-heating is usually conducted for from 5 minutes to 2 hours. A more preferred period is from 5 minutes to about 1 hour.

The post-heating step is conducted to purify the product or raise its purity from that obtained following addition of bromine. Although not bound by any theory, it is believed the post-heating period completes the bromination and increases solubilization of undesired by-products in the liquid phase.

The post-heating time and temperature are not critical so long as they are sufficient for purity enhancement to take place. With a minor amount of experimentation, a skilled practitioner can determine the post-heating time, temperature, and method of obtaining temperature desired for his purpose. Based on such results he may wish to use a temperature or time outside the ranges given above. For example, one may wish to rapidly bring the brominated mixture to post-heating temperature and use a post-heating time prolonged over the periods given above.

Hydrogen bromide can be corrosive in aqueous solution. Accordingly, one may wish to neutralize HBr remaining in the post-heated mass especially if any equipment downstream is excessively corroded by aqueous HBr. Neutralization can be conducted with any alkaline substance. Preferred substances for this invention are sodium hydroxide and sodium carbonate. However, other alkaline materials can be used so long as they are not overly detrimental to the product or reaction vessels. Typical other materials are ammonium acetate, $Ca(OH)_2$, sodium acetate, $NH_3$, lime and sodium bicarbonate. Better results are obtained if the amount of alkaline substance is substantially equal to the amount of HBr present in the post-heated reaction mass. This can be determined by any means available in the art. It is not necessary to use a substantially equivalent amount of alkaline substance. For example, one may use less if it is not desirable or necessary to remove all HBr from the resultant heated reaction mass. One may use more and thereby neutralize a portion of the acetic acid in the reaction mixture. Neutralization of the acetic acid can be uneconomical if it is to be re-used.

EXAMPLE I

A. Bisphenol-A (50 g, 0.219 M) was dissolved in glacial acetic acid (200 ml) and bromine (141 g, 0.88 M) was added at 20°-25° over 53 minutes. The dark red mixture was stirred for 32 minutes, resulting in an orange colored mass having some precipitate. Slow heating was begun; over one hour 55 minutes the temperature was gradually raised to a maximum of 107°, then cooled to room temperature. The granular precipitate was filtered, rinsed once with acetic acid (50 ml) and dried to give a white product (71.1 g, 59.7 percent) with a melting point of 177°-182°.

The filtrate was concentrated to ca. 100 ml, cooled to room temperature, filtered, washed with a small volume of acetic acid and dried to give an off-white second crop (17.3 g, 14.5 percent) having a melting range of 171°-179°.

The filtrate from the second crop was stripped to give an oily residue (36.5 g) which exhibits strong ester absorptions in the infrared region.

B. Bisphenol-A (50 g, 0.219 M) was dissolved in a mixture of glacial acetic acid (190 g) and water (10 g). Bromine (141 g, 0.88 M) was added at 21°-24° over 40 minutes. The mixture was heated to 105° over one hour 2 minutes, then cooled to room temperature under a nitrogen flush. The precipitate was filtered, washed twice with 95 percent acetic acid (100 ml total) and dried to give a white, granular product (97.0 g, 81.5 percent) with melting point 177.5°-181.0°.

The filtrate was concentrated to ca. 100 ml. and cooled to room temperature. The mixture was filtered, washed once with dilute (20 percent) acetic acid, (ca 100 ml) and dried to give an off-white crop (10.0 g, 8.4 percent) melting at 158°-173°.

The filtrate from the second crop was stripped to give 12.6 g of a viscous oil whose infrared spectrum shows acetylated phenolic functionality.

C. Bisphenol-A (50 g, 0.219 M) was dissolved in a mixture of glacial acetic acid (180 g) and water (20 g). Bromine (141 g, 0.88 M) was added at 18°-25° over 40 minutes. Solids began to separate shortly after completion of addition; at this time the mixture was heated to ca 100° over 40 minutes. After 5 minutes at 98°–105°, the mixture was cooled to room temperature, filtered and washed with 90 percent acetic acid (2×50 ml) and then water (2×200 ml). The product was dried to a constant weight of 107.6 g (90.3 percent) with melting point 179.5°–181.5°.

The filtrate, including the acid washes, was concentrated to ca. 75 ml. on the rotary evaporator, then cooled to room temperature, filtered and washed with dilute acetic acid to give (after drying) a tacky, tan solid (9.7 g, 8.15 percent with melting point <140°.

The filtrate from the second crop was stripped to give 1.5 g. of a dark oil with the acetylated phenolic infrared absorptions.

D. Following the general method as above, the reaction was repeated using 85 weight percent acetic acid.

E. Following the general method given above, the reaction was repeated with 90 weight percent glacial acetic acid. The product was washed with two 40 ml. washes of 50 percent acetic acid followed by two 250 ml of $H_2O$.

The results are summarized in the table below:

TABLE I

BROMINATION OF BISPHENOL-A IN ACETIC ACID

|     | BP-A$^a$ Moles | g. | HOAc$^b$ g | $H_2O$ g | Per cent HOAc | Br Moles | g | g | Yield | TBBP-A$^c$ m.p. | f.p. |
|-----|------|----|-----|----|-----|------|-----|-------|------------|-------|
| (A) | 0.219 | 50 | 200 | 0 | 100 | 0.92 | 147 | 71.1 | 59.7$^c$ | 177–182° | — |
| (B) | 0.219 | 50 | 190 | 10 | 95 | 0.88 | 141 | 97.0 | 81.5$^c$ | 177.5–181° | — |
| (C) | 0.219 | 50 | 180 | 20 | 90 | 0.88 | 141 | 107.6 | 90.3$^c$ | 179.5–181.5 | — |
| (D) | 0.219 | 50 | 170 | 30 | 85 | 0.88 | 141 | 112.7 | 94.7$^c$ | 177.5–181.5 | 177.6 |
| (E) | 0.219 | 50 | 180 | 20 | 90 | 0.88 | 141 | 107.4 | 90.3$^c$ | 178–179°* | — |

$^a$bisphenol-A
$^b$acetic acid
$^c$tetrabromobisphenol-A, otherwise known as 4,4'-isopropylidene bis(2,6-dibromophenol)
*melting point 0.5–1.0° C. lower than true value Similar results are obtained using 75 weight percent and 95 weight percent acetic acid. Similar results are obtained using a reaction temperature of 0° to 30° C. Similar results are obtained when the 4,4'-isopropylidene bis(phenol) starting material is replaced with compounds (i)–(x) above. Similar results are obtained using 4–5 moles bromine per mole diphenol.

EXAMPLE II

In a series of experiments, the effect of post-heat treatment was obtained. In this series, 141 grams of bromine was added to 50 grams of 4,4'-isopropylidene bis(phenol) in 200 grams of 85 percent by weight aqueous acetic acid.

In Experiment (F) the brominated reaction mixture was stirred at room temperature for 110 minutes. In Experiments (G)-(I) the post-heat temperature was reached by raising the reaction temperature to 100° C. over a period of 35–45 minutes.

Results are summarized in the following table:

|     | Time at 100–110° (Minutes) | TBBP-A g | Yield | m.p. | f.p. |
|-----|------|-------|------|----------|--------|
| (F) | 0 | 108.4 | 91.2 | 165–179° | 167.9° |
| (G) | 5 | 112.7 | 94.7 | 177.5–181.5 | 177.6° |
| (H) | 60 | 110.0 | 92.3 | 180–182° | 179.1° |
| (I) | 60 | 110.0 | 92.3 | 179–181 * | — |

* melting point 0.5–1.0° C. lower than true value.

Similar results are obtained when the post-heat treatment is conducted at 80° to 120° C. using compounds (i)–(x) above.

EXAMPLE III

A series of experiments was conducted studying the effect of addition of a neutralization agent after the post-heat treatment. In this series, 50 gram portions of bisphenol-A and 141 gram portions of bromine were reacted.

In Run (I) the post-heat period was one hour. In all others a one-half hour period was used. The post-heat temperature for all experiments in the following table was 100°–105° C.

The amount of caustic was added in one batch at about 60° C. The product was washed with one 80 gram portion of 85 percent acetic acid and twice with 250 gram portions of water.

In Run (J), 58.6 grams of acetic acid was added just prior to neutralization to maintain 85 percent HOAc thereby compensating for the water formed on neutralization.

Results are summarized in the following table:

|     | HOAc(g) | $H_2O$(g) | HBr Overhead(g) | NaOH(g) | Rx. Temp. | Yield | APHA Color$^a$ | m.p. °C. | f.p. °C. |
|-----|------|-----|------|------|-------|------|----|-------------|-------|
| (I) | 170 | 30 | 25.0 | 0 | 28–37 | 91.3 | — | 177.0–180.0 | — |
| (J) | 170$^b$ | 30 | 25.0 | 23.0 | 18–24 | 92.4 | 14 | 180.0–181.5 | 179.4 |
| (K) | 170 | 30 | 28.1 | 21.4 | 18–22 | 93.3 | 17 | 179.0–181.5 | 178.7 |
| (L) | 135 | 15 | 54.0 | 3.1$^c$ | 16–23 | 90.0 | 11 | 180.0–182.0 | 179.2 |
| (M) | 135 | 15 | 51.0 | 10.1 | 20–23 | 91.0 | 17 | 180.0–182.0 | 179.2 |

$^a$APHA color obtained by making 10g product up to 100 ml in MeHO. The initial value (Table 2) is reduced by 40–50 per cent after 1.0 hours.
$^b$58.6g HOAc added just prior to NaOH to maintain 85 per cent HOAc.
$^c$Correct amount NaOH should have been 8.5g.

The product in each instance was tetrabromo bisphenol-A.

The HBr overhead is that caught in a trap. The amount of NaOH to be added is calculated before adding. The amount of HBr in the trap is subtracted from the amount theoretically present in the reaction mixture, and from this the number of equivalents of HBr is calculated. An amount of sodium hydroxide equal to the number of equivalents required is then calculated.

The temperature of neutralization is not critical. The neutralizing substance can be added in more than one batch or over a period of time.

Similar results are obtained when $Na_2CO_3$ ammonium acetate, sodium acetate or ammonia is used in place of caustic. One half as much water is formed when using $Na_2CO_3$ than when neutralizing with NaOH.

Similar results are obtained when tetrabrominating compounds (i)-(x) above to form the products analogous to the tetrabromo bisphenol-A.

EXAMPLE IV

Powdered bisphenol-A (100.0 g, 0.430 M) was stirred into a solution of acetic acid (270 g) and water (30 g) and after 25 minutes a solution resulted. Bromine (272 g, 1.76 M) was added at 19°–24° over 32 minutes (external cooling). A slow $N_2$ flush was maintained during the addition. The viscous reaction mixture was then stirred at room temperature for 5 minutes, during which time solid deposition began. The mixture was then heated to 100° over 33 minutes and maintained at 100°–105° for 30 minutes. During this time, it was suspected that a small amount of acetic acid may have been forced past the condenser and into the caustic trap. As the HBr gas volume dropped, the $N_2$ flow was increased to compensate, thus keeping the total gas volume fairly constant.

The heat-treated mixture was then cooled to 80°, when the caustic traps were weighed, showing a net gain of 102.5 g, or 1.27 M HBr.

HBr total: 1.76 M
HBr oh'd.: −1.27 M
HBr in pot: 0.49 M = 19.6 g NaOH.

Sodium hydroxide (19.6 g, 0.49 M) was added quickly at a pot temperature of 60°. The heat of neutralization raised the temperature to a maximum of 90° in 2 minutes. After cooling to 20° C. over ca. 30 minutes, the mixture was filtered, washed with 90 percent HOAc (160 g) and then twice with 250 ml. of $H_2O$. The damp cake (232.5 g) was dried to give tetrabromo bisphenol-A (217.2 g, 91.2 percent).

|  | TBBP-A Anal. |
| --- | --- |
| F.P., ° C. | 178.8 |
| APHA Color | 14 |
| Total Br | 58.0 |
| $H_2O$ | 0.039 |
| Fe | 2 ppm |

The original filtrate and the acetic acid wash were combined and distilled out of a reaction flask equipped with a mechanical stirrer. The first cut was taken until the residual slurry was quite thick. The second cut was then taken until near-dryness of the residue.

The residue remaining in the pot was scraped into a sintered glass funnel and as much liquid as possible was pulled through. After one hour, ca. 8 g of dark, viscous filtrate had been collected, and this soon deposited a precipitate of its own. The residue on the filter was triturated with water, but the undissolved material quickly turned to a gummy semi-solid, preventing clean separation of the inorganic salt. The gum, plus the viscous filtrate (above) were dissolved in benzene, filtered and the insolubles washed with water and added to the original water wash. The total amount of water solution was 315 g. The organic residue amounted to 15.0 g after stripping the benzene.

I claim:

1. Process for producing an alkylidene bis(dibromophenol), said process comprising a bromination step and a post-heating step;
said bromination step comprising reacting bromine and an alkylidene bisphenol having the formula

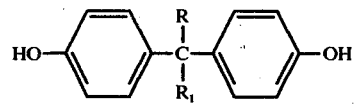

wherein R and $R_1$ are independently selected from the class consisting of hydrogen and alkyl groups of from 1 to about 3 carbons, in a water-acetic acid mixture, the concentration of acetic acid being from about 75 to about 95 weight percent; and said post-heating step comprising subsequently heating the thereby-produced reaction mixture at a temperature of from about 80° to about 120° C. for a period of from about 5 to about 60 minutes.

2. Process of claim 1 wherein alkylidene bisphenol is 4,4′-isopropylidene bis(phenol).

3. Process of claim 2 wherein reaction of said alkylidene bisphenol and bromine is conducted at a temperature within the range of from about 0° to about 30° C.

4. Process of claim 3 wherein said post-heating step is conducted at about 80° – 120° C.

5. Process of claim 4 wherein said post-heating step is conducted for from about 5 to about 60 minutes.

6. A process of claim 1 being further characterized by a neutralization step conducted subsequent to said post-heating step, said neutralization step comprising neutralizing with alkaline substance at least a portion of acid in the heat treated mixture.

7. A process of claim 6 wherein said alkaline substance is selected from the class consisting of sodium hydroxide and sodium carbonate.

8. A process of claim 7 wherein said alkaline substance is sodium carbonate.

9. A process of claim 7 wherein said alkaline substance is sodium hydroxide.

10. A process of claim 6 wherein the amount of alkaline substance is substantially equal to the amount of HBr present in the post-heated reaction mixture.

11. A process for producing tetrabromobisphenol-A, said process comprising
a. brominating bisphenol-A at 20°–30° C. in aqueous acetic acid reaction medium, the concentration of acetic acid in the acetic acid-water mixture being from about 80 to about 90 weight percent, then
b. over a period of about 30 to about 60 minutes, raising the temperature to a post-heating temperature of from about 110°–110° C. and maintaining said post-heating temperature for from about 20 to about 30 minutes, c. subsequently adding an amount of alkaline substance equal to that required to neutralize the HBr present in the heated reaction mixture, said alkaline substance being selected from sodium hydroxide and sodium carbonate, and d. separating the thus-purified tetrabromobisphenol-A, from the alkaline substance-treated reaction mixture.

* * * * *